United States Patent [19]

Luckman et al.

[11] Patent Number: 5,415,663
[45] Date of Patent: May 16, 1995

[54] ORTHOPAEDIC CUTTING GUIDES WITH RETRACTABLE SAW BLADE SLOTS

[75] Inventors: Thomas Luckman, Falmouth; John D. Gundlach, Rowley; Stephen K. Guerrera, Milford, all of Mass.

[73] Assignee: Johnson & Johnson Orthopaedics, Inc., Raynham, Mass.

[21] Appl. No.: 161,113

[22] Filed: Dec. 2, 1993

[51] Int. Cl.⁶ .............................................. A61F 5/00
[52] U.S. Cl. .......................................... 606/86; 606/87
[58] Field of Search ..................... 606/79, 80, 86, 87, 606/88, 96, 97, 98

[56] References Cited

U.S. PATENT DOCUMENTS

| | | | |
|---|---|---|---|
| 4,349,018 | 9/1982 | Chambers | 606/88 |
| 4,565,192 | 1/1986 | Shapiro | 606/88 |
| 4,926,847 | 5/1990 | Luckman | 606/88 |
| 5,053,039 | 1/1991 | Hofmann | 606/86 |
| 5,129,909 | 7/1992 | Sutherland | 606/86 |
| 5,147,365 | 9/1992 | Whitlock | 606/88 |
| 5,275,603 | 1/1994 | Ferrante | 606/86 |

*Primary Examiner*—Michael A. Brown
*Attorney, Agent, or Firm*—Joseph F. Shirtz

[57] ABSTRACT

A new set of surgical instruments is described which provides a movable constraint such that the instruments include a saw guide which may be used in either a constrained or unconstrained fashion. The instruments have a movable restraint which, in the down position provides a continuous surface with the remainder of the instrument for guiding a saw, and when in the up position provides a constrained slot for guiding the saw of a surgeon in making cuts in prosthesis implantation surgery.

8 Claims, 5 Drawing Sheets

ORTHOPAEDIC CUTTING GUIDES WITH RETRACTABLE SAW BLADE SLOTS

FIELD OF THE INVENTION

The invention relates to instruments for performing orthopaedic surgery, and in particular, to guides for guiding saw blades in making cuts in orthopaedic joint replacement.

BACKGROUND OF THE INVENTION

Many types of guide-like instruments are known for orthopaedic surgery. In particular, fixed cutting guides are applied to the exposed bone during knee surgery in order to guide saw cuts of the bone in particular predefined planes.

Currently, not all devices available for aiming or guiding an oscillating saw blade allow the surgeon to achieve a flat, accurate cut unless certain forces are applied to certain surfaces of a cutting block or guide. Devices available with a capturing mechanism for saw blades that will allow for precise bone cuts have fixed slots or guides through which the saw blade passes and is firmly and accurately guided into the correct plane. These devices, although accurate, are generally larger and heavier than devices that do not offer saw blade slots and can actually obscure the surgeon's vision of the saw blade while cutting. Other devices available allow the surgeon to add on guide plates to a flat cutting guide. This is done by assistant while the surgeon attempts to hold the saw blade flat against the cutting surface. The most skilled surgeon who chooses not to use captured cutting guides or finds them cumbersome to use must have a set of guides available to him without slots. This most often means increased instrument inventory and added cost to the hospital as a set of unslotted instruments must be maintained for such surgeons, while slotted instruments are maintained for the remainder of the surgeons.

SUMMARY OF THE INVENTION

The purpose of this invention is to allow the orthopaedic surgeon who desires to make precise bone cuts in the distal femur, proximal tibia and patella to use a single set of instruments which is not dependent on the style of surgery that the surgeon performs.

The solution is to provide the orthopaedic surgeon with the option of using a capturing slot or no slot within the same device without requiring the surgeon to perform the cumbersome task of externally attaching saw guides. The capturing mechanism is built into the cutting block and is retractable. The surgeon who chooses not to use the saw guides simply leaves the blade guide in the retracted position. For those surgeons who prefer captured saw blades, a spring-actuated or manually-actuated capture mechanism may be exposed.

BRIEF DESCRIPTION OF THE DRAWINGS

The invention will now be described with reference to the accompanying drawings wherein.

DETAILED DESCRIPTION OF THE PREFERRED EMBODIMENTS

Standard cutting guides and instruments for performing joint replacement surgery are well-known in the industry. Therefore, in describing this invention, the particular description of materials and attachment mechanisms for instruments will not be described as many manufacturers have already developed such instruments and they are well-known.

Figure 1:
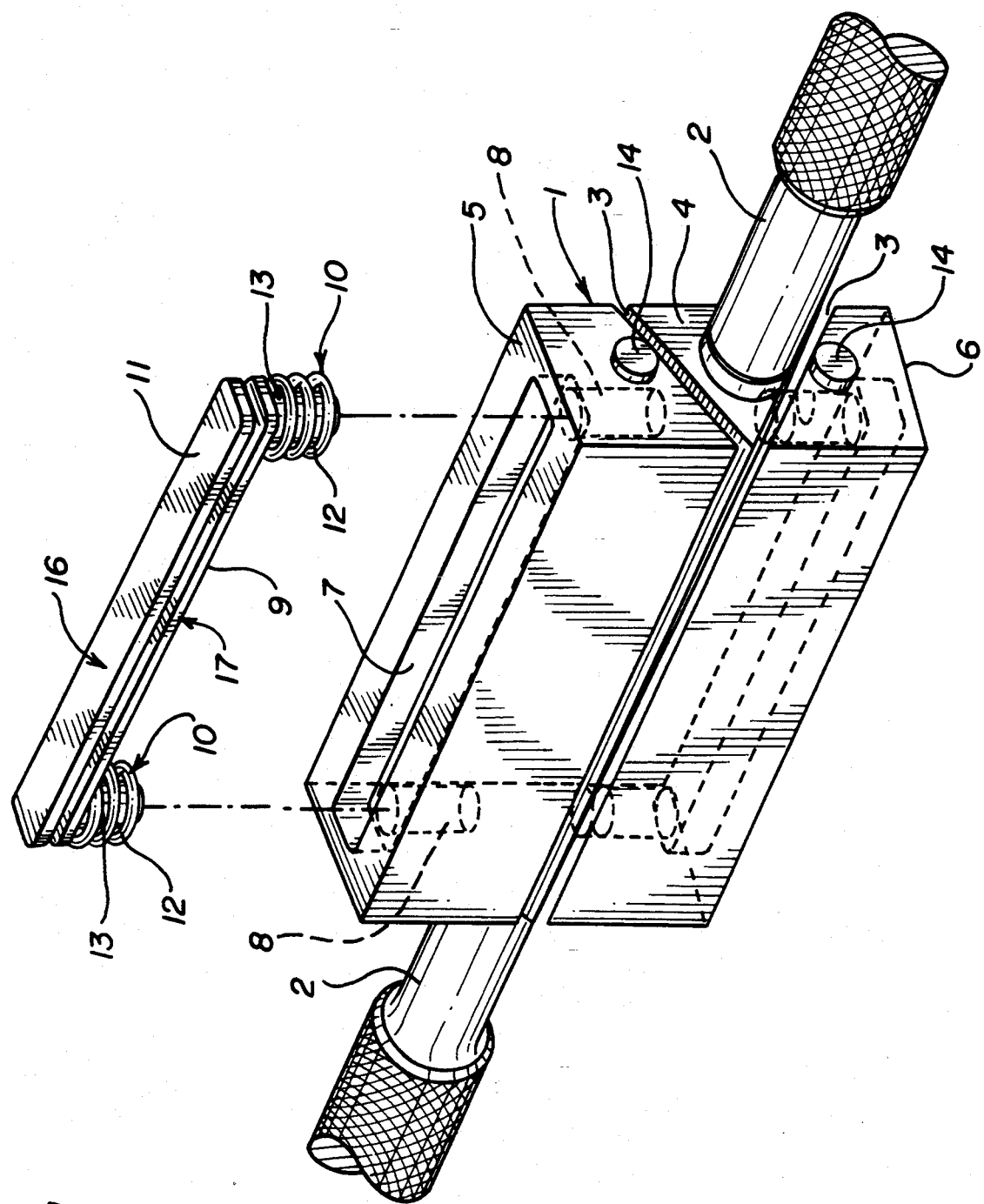
FIG. 1 is a partially exploded view of a chamfer cutting block for making distal femoral cuts in knee replacement surgery.

Referring to FIG. 1, there is shown a representative anterior/posterior chamfer cutting block which is placed transverse to the axis of the femur at a position on the distal femur to guide a saw blade in making the anterior/posterior chamfer cuts as well as the anterior and posterior cuts to prepare the femur for receipt of a prosthesis. A cutting guide 1 is shown having handles 2 to assist in the placement and stabilizing of the cutting guide. A pair of chamfer slots 3 are provided through the cutting guide to guide the saw blade of a surgeon's saw in making the appropriate chamfer cuts on the distal femur. The block has a body 4 and an anterior surface 5 and posterior surface 6.

Anterior surface 5 and posterior surface 6 provide a surface for guiding a saw blade in making the anterior and posterior cuts to the distal femur. Each of the anterior surface 5 and posterior surface 6 are provided with a trough 7 defined by the surface. The trough has a pair of legs defined further by the body 4 of the cutting guide 1 which are cylindrical and extend downward from the base of the trough. The trough 7 is of sufficient dimensions to receive restraint 9 and spring mechanism 10 of restraint 9, such that an upper surface 11 of the restraint 9 is coplanar with the anterior surface 5 or posterior surface 6 as the case may be. A pair of springs 12 surround posts 13 which depend from a bottom of the restraint. Posts 13 are received within legs 8 with springs 12 seated on the bottom of the legs 8. This is more clearly shown with reference to FIGS. 2 and 3. As may be seen in FIG. 2, the legs 8 may be made of multiple diameters. A first larger diameter for receiving the springs 12 and forming a ledge to seat the springs thereon, and a second smaller diameter further depending from the first diameter portion to receive the sliding motion of the posts 13.

The restraint may be held in its lowered position against the urging force of the springs 12 by any suitable restraint means. For example, a pawl 14 may be provided which rides within a detent 15 in the post. The pawl interferes with the sliding relationship of the posts within the leg 8 preventing movement of the restraint from the down position to the up position. Once the pawl is moved out of engagement with the detent the restraint moves in response to the urging force of the spring into the up position. Suitable restraint mechanism of a reasonable form may be provided to prevent the restraint from popping up beyond the preferred up position. The restraint 9 is preferably formed of a two-piece guide which defines a guide slot therethrough. The two-piece guide is formed of an upper slot constraint 16 and a lower slot constraint 17. These two pieces of the restraint run substantially parallel to one another and form the constrained guide slot of the invention. The upper slot constraint has an upper surface that is coplanar with the remainder of the anterior surface 5 or posterior surface 6, as the case may be, when the restraint is received in the down position retracted into the surface of the cutting guide. Thus the cutting guide has a continuous anterior and posterior surface when desired.

Figure 2:
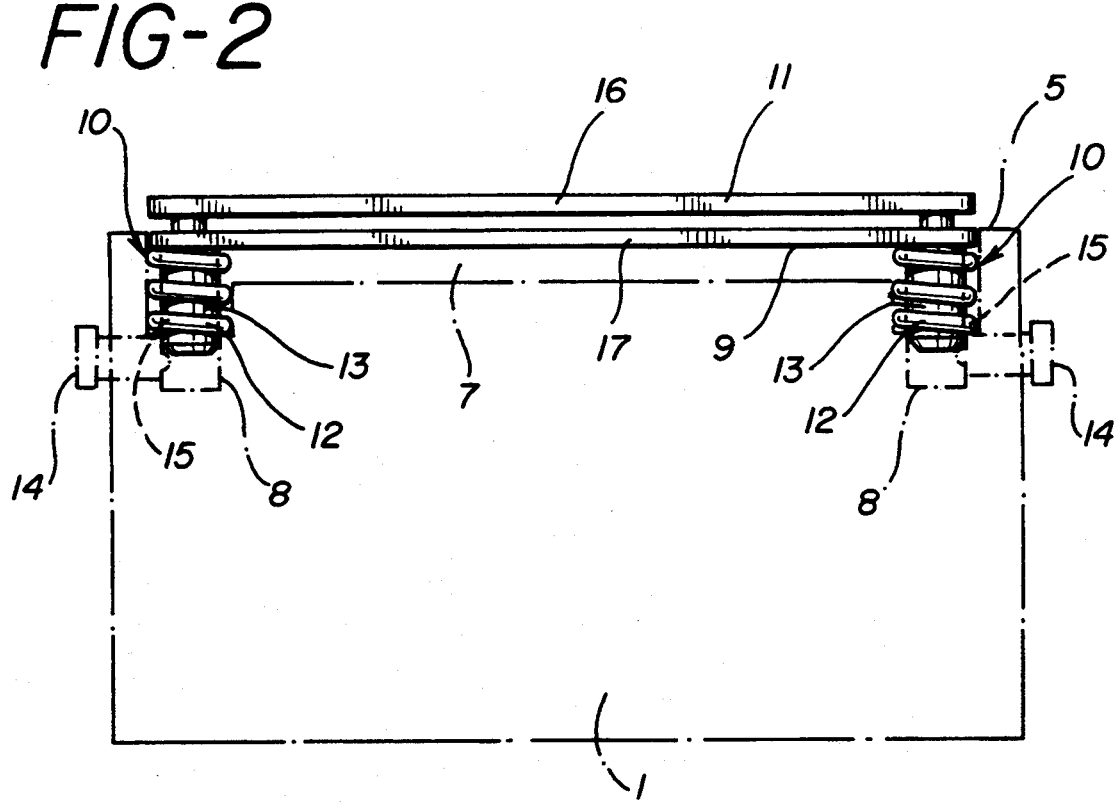
FIG. 2 is a view of the cutting guide of FIG. 1 showing the guide in the up position.
Figure 3:
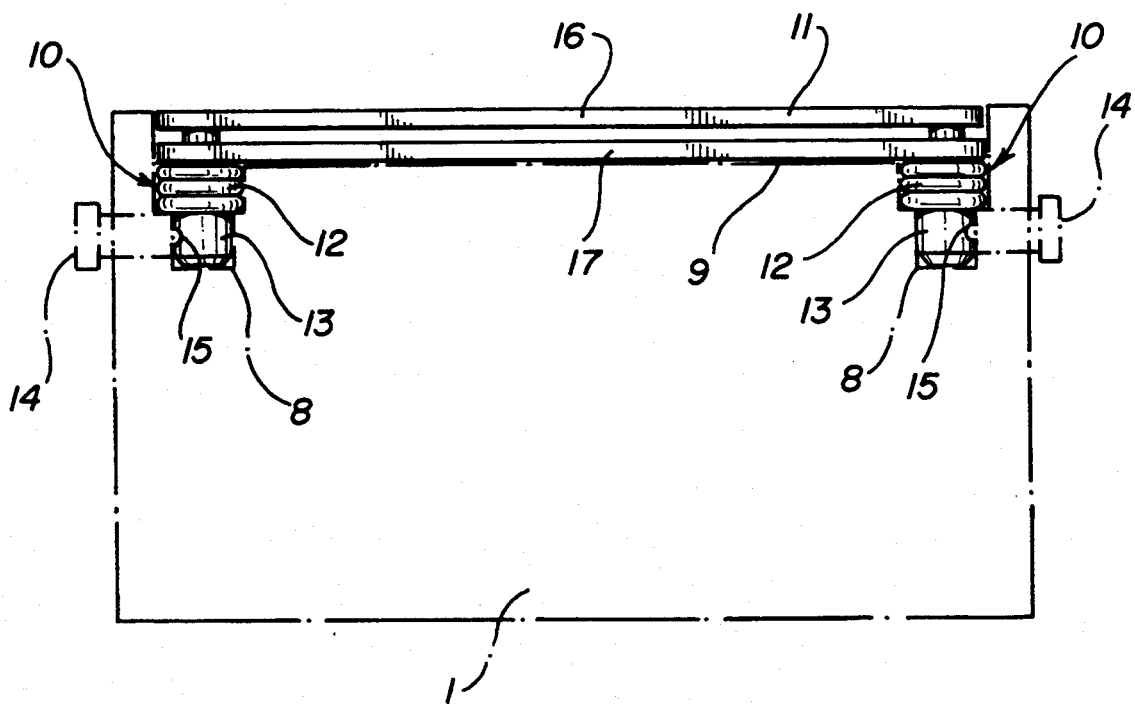
FIG. 3 is a view of the cutting guide of FIG. 1 showing the guide in the down position.

When the restraint 9 is in the up position, the lower slot constraint 17 has an upper surface which is coplanar with either the anterior or posterior surface as the case may be. This provides a smooth coplanar surface for the saw to ride upon while the upper slot constraint prevents movement of the saw blade in the Z direction which is a direction upward in FIG. 2. Thus the saw is constrained from movement in the up/down direction as seen in FIG. 2, but may be moved into and out of the plane to provide an appropriate saw cut.

Figure 4:
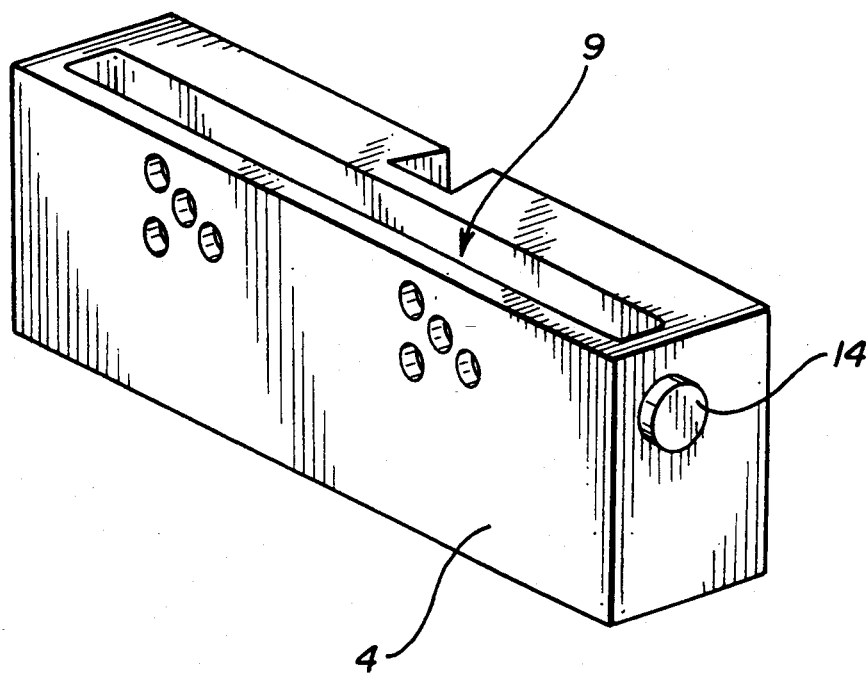
FIG. 4 is a perspective view of a distal femoral cutting block.

Substantially similar constraint means may be provided in other types of cutting blocks. For example, FIG. 4 shows a distal femoral cutting block which is used to guide a saw cut providing the transverse distal femoral cut in knee replacement surgery. The block has a body 4 and a restraint 9 received therein. The restraint 9 is similar to that previously described and may be moved between an up position (not shown) and a down position as shown in FIG. 4.

Figure 5:
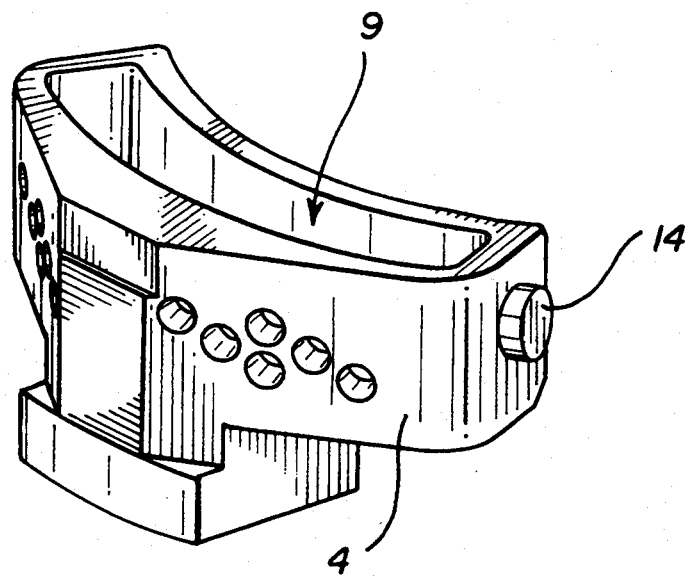
FIG. 5 is a perspective view of a tibial cutting block.
Figure 6:
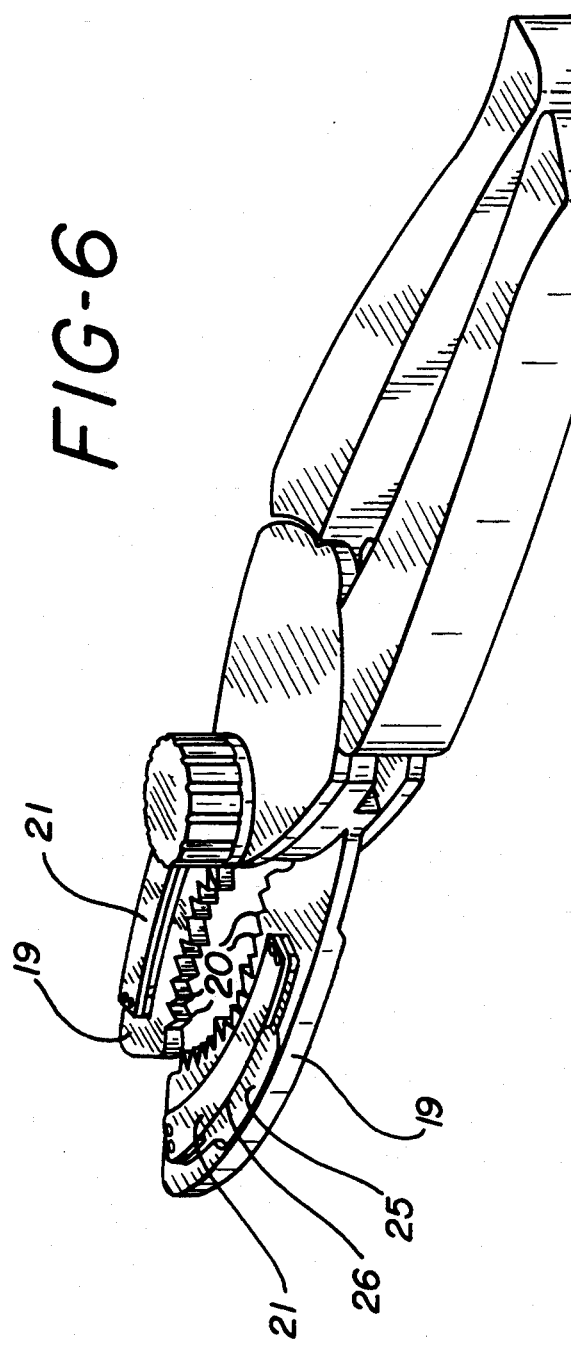
FIG. 6 is a perspective view of a patella clamp for guiding patella cuts.

Similarly, a tibial cutting block for providing a transverse tibial cut is shown in FIG. 5. A restraint 9 similar to that previously described is provided in the upper surface of the tibial cutting block. The only significant difference being that the restraint has a curved planar section. That is, the guide is planar in the direction of the saw cut, but is curved along the anterior surface of the tibia.

Referring now to FIGS. 6-9, a patella clamp for providing a transverse cut to a patella in knee prosthesis implantation surgery is shown. The clamp, in its grabbing portion, is substantially similar to those known in the art. The clamp has a set of jaws 19 with teeth 20 formed thereon. The clamp is biased such that the jaws are biased towards one another to grasp a patella there between. The patella is placed in an appropriate position to be resected via a saw cut on the surface of the jaw.

Figure 7:
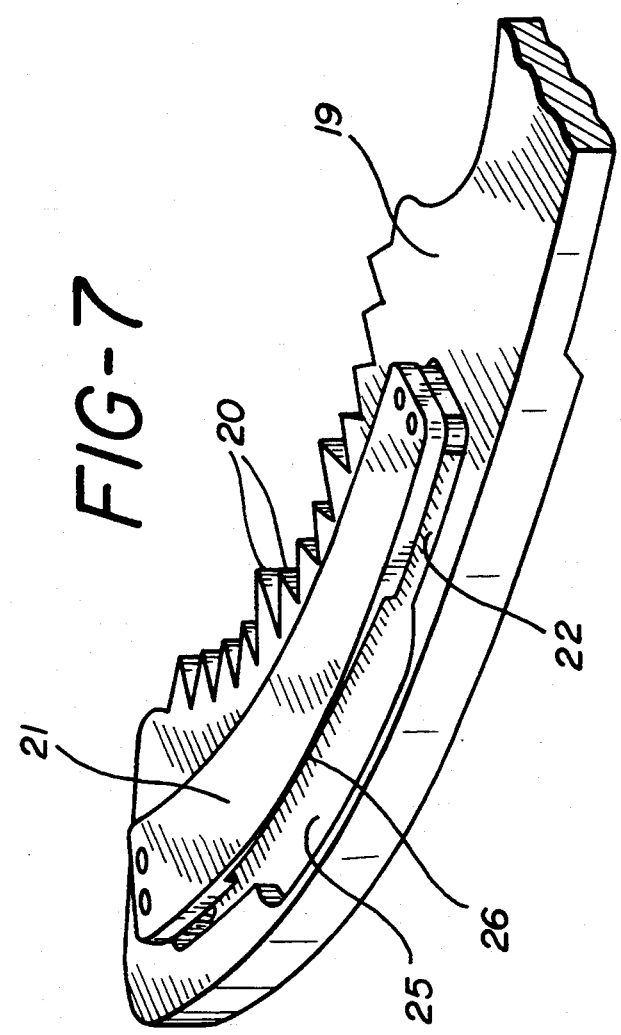
FIG. 7 is a partial perspective view of the clamp of FIG. 6.
Figure 8:
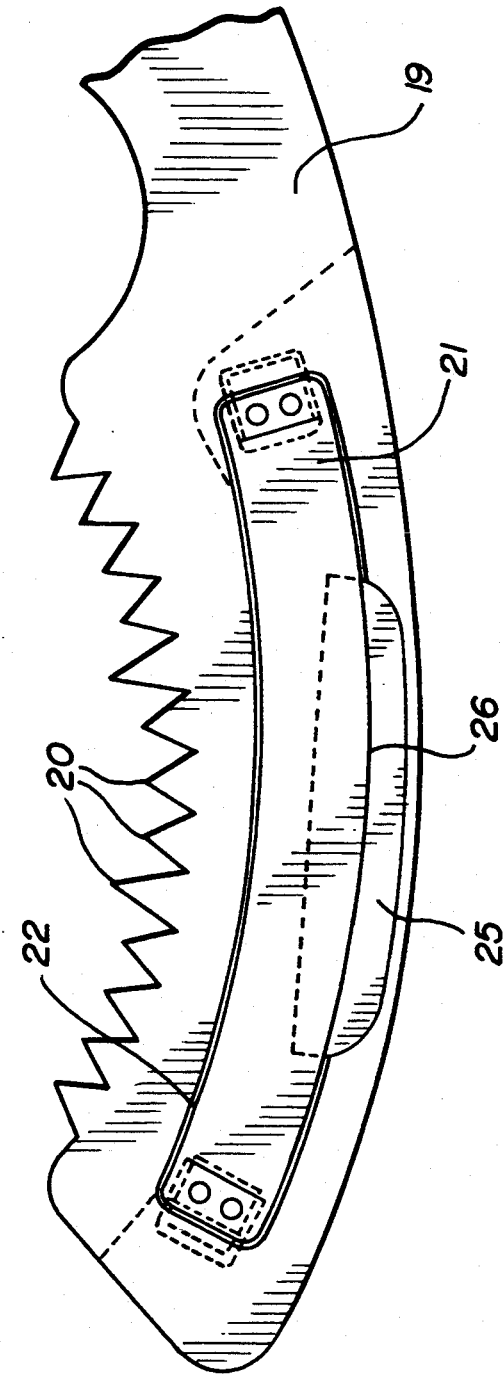
FIG. 8 is a cross-sectional view of the clamp of FIG. 6 showing the guide in the up position.

A single jaw is shown in enlarged condition in FIG. 7. There the jaw 19 has a jaw restraint 21 formed therein. The jaw restraint 21 may be moved between a down position (FIG. 9) and an up position (FIG. 8). This forms a device similar to those described before in which the jaw restraint 21 may be received within a trough 22 formed to permit receipt of the jaw restraint 21 therein to form a substantially continuous surface for guiding a saw. When the jaw restraint is in the "up position" a slot 23 is defined by the jaw restraint and the upper surface of the jaw. This slot provides the constrained guide for the saw when making the patella cut. A pair of posts 24 are provided at the ends of the jaw restraint 21 to provide for the translational movement of the jaw restraint. These posts are received in cut out legs defined within the jaws similar to those described previously. Referring to FIG. 8, it is seen that when the jaw restraint is in the up position, the post depending from a lower surface of the jaw restraint mount the jaw restraint to the surface of the jaw. In this fashion a slot is formed between the jaw restraint and the upper surface of the jaw in order to constrain the guidance of the saw.

Figure 9:
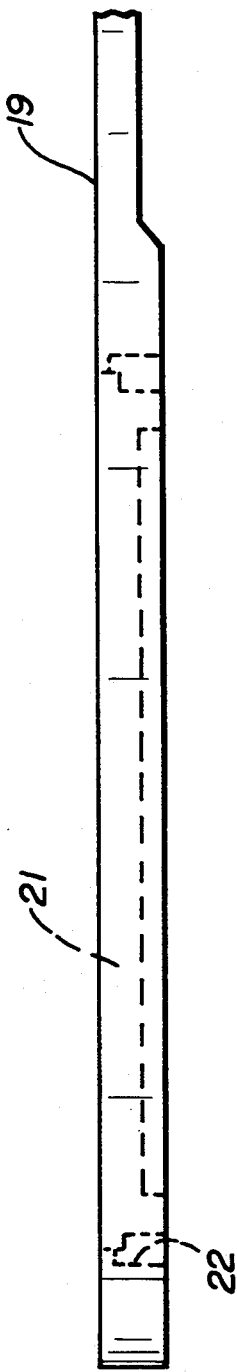
FIG. 9 is a partial cross-sectional view of the clamp of FIG. 6 showing the guide in the down position.

When the jaw restraint is in the down position as shown in FIG. 9, a substantially continuous surface is formed to permit guidance of the saw blade by only the surface contact of the blade and the jaw surface. One difference between the embodiment of the patella clamp and the embodiment described previously is that in this embodiment the jaw defines a partial cutout 25 and the restraint has formed thereon a prying lip 26. When the jaw restraint is in the lower position, the cutout 25 and lip 26 provide access for an instrument to pry up the jaw restraint 21 thus eliminating the need for a spring mechanism and the difficulties in sterilizing that such complex products may provide.

The invention has now been described in detail and will be claimed according to the accompanied claims. However, it is understood by those of skill in the art that equivalent changes may be made to the products without exceeding the scope or spirit of the present invention.

We claim:

1. An instrument for guiding saw cuts in orthopaedic surgery comprising:
   A) means for mounting said instrument in a predetermined position relative a bone to be resected;
   B) a first guide surface providing a substantially unconstrained guide for positioning a saw blade at a particular orientation with respect to said bone; and
   C) a second guide for positioning a saw blade in substantially the same position and orientation as said first guide surface, in a constrained manner.

2. An instrument according to claim 1 wherein:
   A) said second guide comprises a second surface substantially coplanar with said first guide surface and spaced constraint restricting movement of said saw blade in a direction perpendicular to said surface.

3. An instrument according to claim 2 wherein said spaced constraint is movable between a first position wherein said spaced constraint restricts movement of said saw blade in a direction perpendicular to said surface and a second position wherein said spaced constraint forms part of said first guide surface.

4. An instrument for orthopaedic surgery comprising:
   A) means for positioning said instrument in a fixed predetermined position with respect to a bone to be cut;
   B) a guide surface for guiding a saw blade at a predetermined position and orientation with respect to said bone; and
   C) constraint means movable between a first position constraining substantial movement of said saw blade in a first direction while in said predetermined position and orientation and a second position permitting such saw blade to move in said first direction when said saw blade is in said predetermined position and orientation.

5. The instrument according to claim 4 wherein said constraint means is received within said instrument to partially define said guide surface when said constraint means is in said second position.

6. The instrument according to claim 5 wherein said constraint means has a first and a second surface in spaced parallel relationship and said first surface partially forms said guide surface when said constraint means is in said first position and said second surface partially forms said guide surface when said constraint means is in said second.

7. The instrument according to claim 6 wherein said instrument includes a body at least partially defining an opening for receiving a portion of said constraint means when said constraint means is in said second position.

8. The instrument according to claim 7 wherein said constraint means includes a pair of substantially parallel plates, each plate presenting a respective upper surface that respectively at least partially define said first and second surface.

* * * * *